(12) United States Patent
Zhang et al.

(10) Patent No.: US 10,395,356 B2
(45) Date of Patent: Aug. 27, 2019

(54) GENERATING SIMULATED IMAGES FROM INPUT IMAGES FOR SEMICONDUCTOR APPLICATIONS

(71) Applicant: KLA-Tencor Corporation, Milpitas, CA (US)

(72) Inventors: Jing Zhang, Santa Clara, CA (US); Kris Bhaskar, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/603,249

(22) Filed: May 23, 2017

(65) Prior Publication Data

US 2017/0345140 A1 Nov. 30, 2017

Related U.S. Application Data

(60) Provisional application No. 62/341,548, filed on May 25, 2016.

(51) Int. Cl.
*G06T 7/00* (2017.01)

(52) U.S. Cl.
CPC .. *G06T 7/0004* (2013.01); *G06T 2207/20081* (2013.01); *G06T 2207/20084* (2013.01); *G06T 2207/30148* (2013.01)

(58) Field of Classification Search
CPC ........ G06T 7/0004; G06T 2207/20081; G06T 2207/20084; G06T 2207/30148
See application file for complete search history.

(56) References Cited

U.S. PATENT DOCUMENTS

| | | | |
|---|---|---|---|
| 6,622,135 B1 * | 9/2003 | Imbert De Tremiolles | G06K 9/6276 706/20 |
| 7,570,796 B2 | 8/2009 | Zafar et al. | |
| 7,676,077 B2 | 3/2010 | Kulkarni et al. | |
| 8,126,255 B2 | 2/2012 | Bhaskar et al. | |
| 8,294,918 B2 | 10/2012 | Satoh et al. | |
| 8,664,594 B1 | 4/2014 | Jiang et al. | |

(Continued)

FOREIGN PATENT DOCUMENTS

| | | |
|---|---|---|
| JP | 2005-338666 | 12/2005 |
| WO | 2006/019919 | 2/2006 |
| WO | 2011/096136 | 8/2011 |

OTHER PUBLICATIONS

Mairal, J., Koniusz, P., Harchaoui, Z., & Schmid, C. (2014). Convolutional kernel networks. In Advances in neural information processing systems (pp. 2627-2635 (Year: 2014).*

(Continued)

*Primary Examiner* — Menatoallah Youssef
(74) *Attorney, Agent, or Firm* — Ann Marie Mewherter

(57) ABSTRACT

Methods and systems for generating a simulated image from an input image are provided. One system includes one or more computer subsystems and one or more components executed by the one or more computer subsystems. The one or more components include a neural network that includes two or more encoder layers configured for determining features of an image for a specimen. The neural network also includes two or more decoder layers configured for generating one or more simulated images from the determined features. The neural network does not include a fully connected layer thereby eliminating constraints on size of the image input to the two or more encoder layers.

27 Claims, 6 Drawing Sheets

(56) References Cited

U.S. PATENT DOCUMENTS

| | | | |
|---|---|---|---|
| 8,692,204 | B2 | 4/2014 | Kojima et al. |
| 8,698,093 | B1 | 4/2014 | Gubbens et al. |
| 8,716,662 | B1 | 5/2014 | MacDonald et al. |
| 9,222,895 | B2 | 12/2015 | Duffy et al. |
| 2008/0255786 | A1 | 10/2008 | Jin et al. |
| 2016/0116420 | A1 | 4/2016 | Duffy et al. |
| 2016/0372303 | A1 | 12/2016 | Park et al. |
| 2016/0377425 | A1 | 12/2016 | Gupta et al. |
| 2018/0107928 | A1* | 4/2018 | Zhang .............. G06K 9/46 |

OTHER PUBLICATIONS

Srinivas, Suraj, et al. "A taxonomy of deep convolutional neural nets for computer vision." Frontiers in Robotics and AI 2 (2016): 36. (Year: 2016).*

Bian X, Lim SN, Zhou N. Multiscale fully convolutional network with application to industrial inspection. In Applications of Computer Vision (WACV), 2016 IEEE Winter Conference on Mar. 7, 2016(pp. 1-8). IEEE (Year: 2016).*

Goodfellow et al., "Generative Adversarial Nets," arXiv:1406.2661, Jun. 10, 2014, 9 pages.

Hand et al., "Principles of Data Mining (Adaptive Computation and Machine Learning)," MIT Press, Aug. 1, 2001, 578 pages.

International Search Report and Written Opinion for PCT/US2017/034322 dated Aug. 11, 2017.

Jebara, "Discriminative, Generative, and Imitative Learning," MIT Thesis, Feb. 2002, 212 pages.

Long et al., "Fully convolutional networks for semantic segmentation," 2015 IEEE Conference on Computer Vision and Pattern Recognition, Jun. 7-12, 2015, pp. 3431-3440.

Makhzani et al., "Adversarial Autoencoders," arXiv:1511.05644v2, May 25, 2016, 16 pages.

Mirza et al., "Conditional Generative Adversarial Nets," arXiv:1411.1784, Nov. 6, 2014, 7 pages.

Sugiyama, "Introduction to Statistical Machine Learning," Morgan Kaufmann, Oct. 9, 2015, 534 pages.

U.S. Appl. No. 15/176,139 by Zhang et al. filed Jun. 7, 2016 (submitted as U.S. Patent Application Publication No. 2017/0148226 published May 25, 2017).

U.S. Appl. No. 15/353,210 by Karsenti et al. filed Nov. 16, 2016 (submitted as U.S. Patent Application Publication No. 2017/0140524 published May 18, 2017).

U.S. Appl. No. 15/394,790 by Bhaskar et al. filed Dec. 29, 2016 (submitted as U.S. Patent Application Publication No. 2017/0193400 published Jul. 6, 2017).

U.S. Appl. No. 15/394,792 by Bhaskar et al. filed Dec. 29, 2016 (submitted as U.S. Patent Application Publication No. 2017/0194126 published Jul. 6, 2017).

U.S. Appl. No. 15/396,800 by Zhang et al. filed Jan. 2, 2017 (submitted as U.S. Patent Application Publication No. 2017/0193680 published Jul. 6, 2017).

U.S. Appl. No. 15/402,094 by Bhaskar et al. filed Jan. 9, 2017 (submitted as U.S. Patent Application Publication No. 2017/0200265 published Jul. 13, 2017).

U.S. Appl. No. 15/402,169 by Bhaskar et al. filed Jan. 9, 2017 (submitted as U.S. Patent Application Publication No. 2017/0200260 published Jul. 13, 2017).

U.S. Appl. No. 15/402,197 by Park et al. filed Jan. 9, 2017 (submitted as U.S. Patent Application Publication No. 2017/0200264 published Jul. 13, 2017).

* cited by examiner

GENERATING SIMULATED IMAGES FROM INPUT IMAGES FOR SEMICONDUCTOR APPLICATIONS

BACKGROUND OF THE INVENTION

1. Field of the Invention

The present invention generally relates to methods and systems for generating simulated images from input images for semiconductor applications.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on specimens to drive higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Defect review typically involves re-detecting defects detected as such by an inspection process and generating additional information about the defects at a higher resolution using either a high magnification optical system or a scanning electron microscope (SEM). Defect review is therefore performed at discrete locations on specimens where defects have been detected by inspection. The higher resolution data for the defects generated by defect review is more suitable for determining attributes of the defects such as profile, roughness, more accurate size information, etc.

Metrology processes are also used at various steps during a semiconductor manufacturing process to monitor and control the process. Metrology processes are different than inspection processes in that, unlike inspection processes in which defects are detected on specimens, metrology processes are used to measure one or more characteristics of the specimens that cannot be determined using currently used inspection tools. For example, metrology processes are used to measure one or more characteristics of specimens such as a dimension (e.g., line width, thickness, etc.) of features formed on the specimens during a process such that the performance of the process can be determined from the one or more characteristics. In addition, if the one or more characteristics of the specimens are unacceptable (e.g., out of a predetermined range for the characteristic(s)), the measurements of the one or more characteristics of the specimens may be used to alter one or more parameters of the process such that additional specimens manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at which a metrology process is performed on specimens may be independent of the results of an inspection process performed on the specimens. In particular, the locations at which a metrology process is performed may be selected independently of inspection results.

As design rules shrink, the design that is formed on a specimen such as reticles and wafers, even when formed using an optimally performing process, can look much different from the actual design. For example, due to the inherent limitations of the physical processes involved in forming a design on a physical specimen, features in the design formed on the physical specimen typically have somewhat different characteristics than the design such as different shapes (e.g., due to corner rounding and other proximity effects) and can have somewhat different dimensions (e.g., due to proximity effects) even when the best possible version of the design has been formed on the specimen.

Sometimes, it is not possible to know how the design will appear on the specimen and in images of the specimen, on which the design information has been formed, generated by tools such as inspection tools, defect review tools, metrology tools and the like. However, it is often desirable to know how the design will appear on the specimen and in images generated by such tools for a number of reasons. One reason is to make sure that the design be formed on the specimen in an acceptable manner. Another reason is to provide a reference for the design, which illustrates how the design is meant to be formed on the specimen, that can be used for one or more functions performed for the specimen. For example, in general, a reference is needed for defect detection so that any differences between the design formed on the specimen and the reference can be detected and identified as defects or potential defects.

Much work has therefore been done to develop various methods and systems that can simulate one image for a specimen from another image for the specimen. There are, however, several disadvantages to the currently available methods. For example, some currently used methods have upper limits on the sizes of the input images that the methods can transform. Other currently used methods can transform substantially large input images but do so with several disadvantages.

In one such example, one currently used method for transforming relatively large input images includes cropping the (relatively large) arbitrarily sized image (e.g., 1024 pixels by 1024 pixels) into many image patches with the required size (e.g., 64 pixels by 64 pixels), then feeding all the patches through a neural network. The image-sized (i.e., 1024 pixels by 1024 pixels) result may be constructed from the patch-sized results (i.e., 923,521 image patches, each having a size of 64 pixels by 64 pixels).

There are, therefore, several disadvantages to such currently used methods. For example, the currently used methods require enormous amounts of computation at runtime (e.g., processing a 1024 pixel by 1024 pixel image requires tens of minutes to several hours) even on the fastest graphics processing unit (GPU). In addition, the currently used methods include extra cropping and reconstructing steps, which complicate the software implementation flow.

Accordingly, it would be advantageous to develop systems and methods for generating simulated images from input images that do not have one or more of the disadvantages described above.

SUMMARY OF THE INVENTION

The following description of various embodiments is not to be construed in any way as limiting the subject matter of the appended claims.

One embodiment relates to a system configured to generate a simulated image from an input image. The system includes one or more computer subsystems and one or more components executed by the one or more computer subsystems. The one or more components include a neural network that includes two or more encoder layers configured for determining features of an image for a specimen. The neural network also includes two or more decoder layers configured for generating one or more simulated images from the determined features. The neural network does not include a fully connected layer thereby eliminating constraints on size of the image input to the two or more encoder layers. The system may be further configured as described herein.

An additional embodiment relates to another system configured to generate a simulated image from an input image. This system is configured as described above. This system also includes an imaging subsystem configured for generating an image of a specimen that is input to the two or more encoder layers. The computer subsystem(s) are, in this embodiment, configured for acquiring the image from the imaging subsystem. This embodiment of the system may be further configured as described herein.

Another embodiment relates to a computer-implemented method for generating a simulated image from an input image. The method includes acquiring an image for a specimen. The method also includes determining features of the image for the specimen by inputting the image into two or more encoder layers of a neural network. In addition, the method includes generating one or more simulated images from the determined features. Generating the one or more simulated images is performed by two or more decoder layers of the neural network. The acquiring, determining, and generating are performed by one or more computer systems. One or more components are executed by the one or more computer systems, and the one or more components include the neural network.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on one or more computer systems for performing a computer-implemented method for generating a simulated image from an input image. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
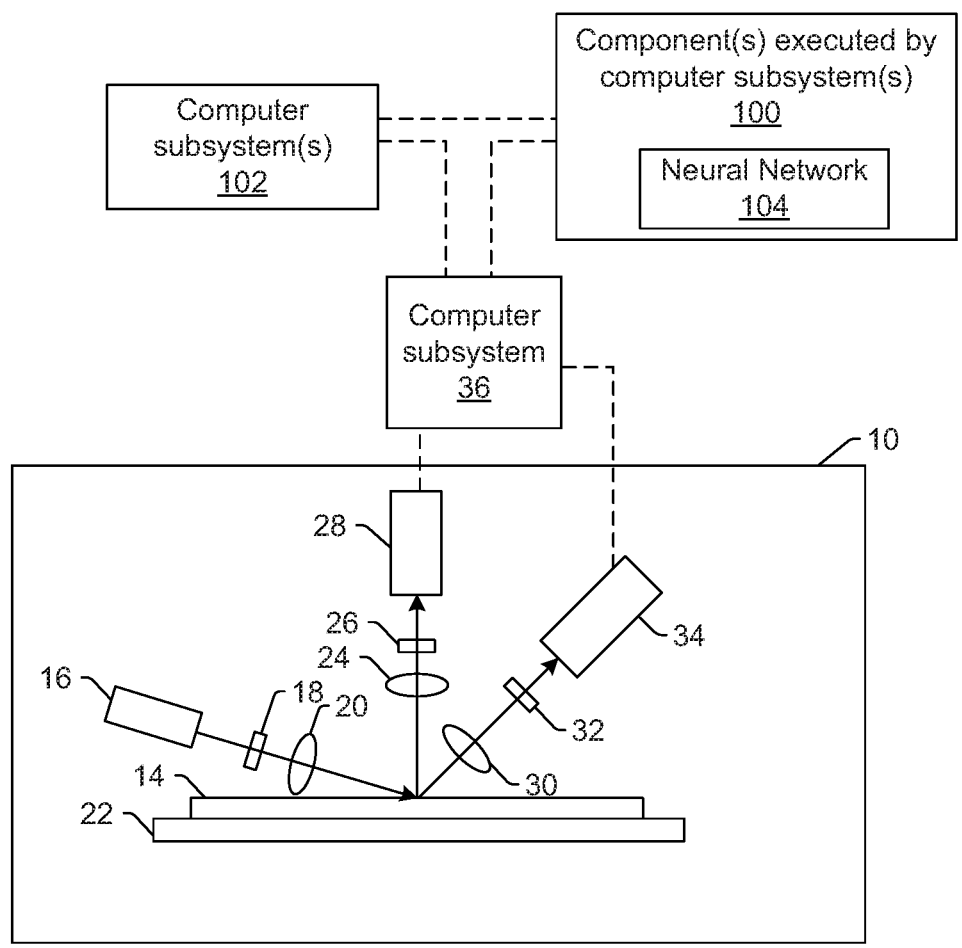
FIGS. 1 and 1a are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design," "design data," and "design information" as used interchangeably herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In addition, the "design," "design data," and "design information" described herein refers to information and data that is generated by semiconductor device designers in a design process and is therefore available for use in the embodiments described herein well in advance of printing of the design on any physical specimens such as reticles and wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to generate a simulated image from an input image. In general, the embodiments described herein may be configured as fully convolutional deep generative models for semiconductor inspection and metrology applications. The embodiments described herein advantageously provide a computationally efficient methodology for (1) enabling a deep generative model computable on arbitrarily sized images and (2) tremendously reducing the computational time for runtime prediction by 100× to 1000×, possibly for optical, electron beam, wafer, mask, inspection, and metrology tools.

One embodiment of a system configured to generate a simulated image from an input image is shown in FIG. 1. The system includes one or more computer subsystems (e.g., computer subsystem 36 and computer subsystem(s) 102) and one or more components 100 executed by the one or more computer subsystems. In some embodiments, the system includes imaging system (or subsystem) 10. In the embodiment of FIG. 1, the imaging system is configured for scanning light over or directing light to a physical version of the specimen while detecting light from the specimen to thereby generate the images for the specimen. The imaging system may also be configured to perform the scanning (or directing) and the detecting with multiple modes.

In one embodiment, the specimen is a wafer. The wafer may include any wafer known in the art. In another embodiment, the specimen is a reticle. The reticle may include any reticle known in the art.

In one embodiment, the imaging system is an optical based imaging system. In this manner, in some embodiments, the image input to the two or more encoder layers described further herein is generated by an optical based imaging system. In one such example, in the embodiment of the system shown in FIG. 1, optical based imaging system 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to specimen 14 at an oblique angle of incidence. The oblique angle of incidence may include any suitable oblique angle of incidence, which may vary depending on, for instance, characteristics of the specimen.

The imaging system may be configured to direct the light to the specimen at different angles of incidence at different times. For example, the imaging system may be configured to alter one or more characteristics of one or more elements of the illumination subsystem such that the light can be directed to the specimen at an angle of incidence that is different than that shown in FIG. 1. In one such example, the imaging system may be configured to move light source 16, optical element 18, and lens 20 such that the light is directed to the specimen at a different oblique angle of incidence or a normal (or near normal) angle of incidence.

In some instances, the imaging system may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused onto specimen 14 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the imaging system may be configured to alter one or more of the elements of the illumination subsystem based on the type of illumination to be used for imaging.

The imaging system may also include a scanning subsystem configured to cause the light to be scanned over the specimen. For example, the imaging system may include stage 22 on which specimen 14 is disposed during inspection. The scanning subsystem may include any suitable mechanical and/or robotic assembly (that includes stage 22) that can be configured to move the specimen such that the light can be scanned over the specimen. In addition, or alternatively, the imaging system may be configured such that one or more optical elements of the imaging system perform some scanning of the light over the specimen. The light may be scanned over the specimen in any suitable fashion such as in a serpentine-like path or in a spiral path.

The imaging system further includes one or more detection channels. At least one of the one or more detection channels includes a detector configured to detect light from the specimen due to illumination of the specimen by the system and to generate output responsive to the detected light. For example, the imaging system shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect light that is scattered at different angles from the specimen. However, one or more of the detection channels may be configured to detect another type of light from the specimen (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the imaging system that includes two detection channels, the imaging system may include a different number of detection channels (e.g., only one detection channel or two or more detection channels). In one such instance, the detection channel formed by collector 30, element 32, and detector 34 may form one side channel as described above, and the imaging system may include an additional detection channel (not shown) formed as another side channel that is positioned on the opposite side of the plane of incidence. Therefore, the imaging system may include the detection channel that includes collector 24, element 26, and detector 28 and that is centered in the plane of incidence and configured to collect and detect light at scattering angle(s) that are at or close to normal to the specimen surface. This detection channel may therefore be commonly referred to as a "top" channel, and the imaging system may also include two or more side channels configured as described above. As such, the imaging system may include at least three channels (i.e., one top channel and two side channels), and each of the at least three channels has its own collector, each of which is configured to collect light at different scattering angles than each of the other collectors.

As described further above, each of the detection channels included in the imaging system may be configured to detect scattered light. Therefore, the imaging system shown in FIG. 1 may be configured for dark field (DF) imaging of specimens. However, the imaging system may also or alternatively include detection channel(s) that are configured for bright field (BF) imaging of specimens. In other words, the imaging system may include at least one detection channel that is configured to detect light specularly reflected from the specimen. Therefore, the imaging systems described herein may be configured for only DF, only BF, or both DF and BF imaging. Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), time delay integration (TDI) cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity hut may not be configured to detect such characteristics as a function of position within the imaging plane. As such, the output that is generated by each of the detectors included in each of the detection channels of the imaging system may be signals or data, but not image signals or image data. In such instances, a computer subsystem such as computer subsystem 36 may be configured to generate images of the specimen from the non-imaging output of the detectors. However, in other instances, the detectors may be configured as imaging detectors that are configured to generate image signals or image data. Therefore, the imaging system may be configured to generate the images described herein in a number of ways.

It is noted that FIG. 1 is provided herein to generally illustrate a configuration of an imaging system or subsystem that may be included in the system embodiments described herein or that may generate images that are used by the system embodiments described herein. Obviously, the imaging system configuration described herein may be altered to optimize the performance of the imaging system as is normally performed when designing a commercial imaging system. In addition, the systems described herein may be implemented using an existing system (e.g., by adding functionality described herein to an existing system) such as the 29xx/39xx and Puma 9xxx series of tools that are commercially available from KLA-Tencor, Milpitas, Calif. For some such systems, the embodiments described herein may be provided as optional functionality of the system (e.g., in addition to other functionality of the system). Alternatively, the imaging system described herein may be designed "from scratch" to provide a completely new imaging system.

Computer subsystem 36 of the imaging system may be coupled to the detectors of the imaging system in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number of functions described further herein using the output of the detectors.

The computer subsystems shown in FIG. 1 (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 as shown by the dashed line in FIG. 1 by any suitable transmission media, which may include any suitable wired and/or wireless transmission media known in the art. Two or more of such computer subsystems may also be effectively coupled by a shared computer-readable storage medium (not shown).

Figure 1A:
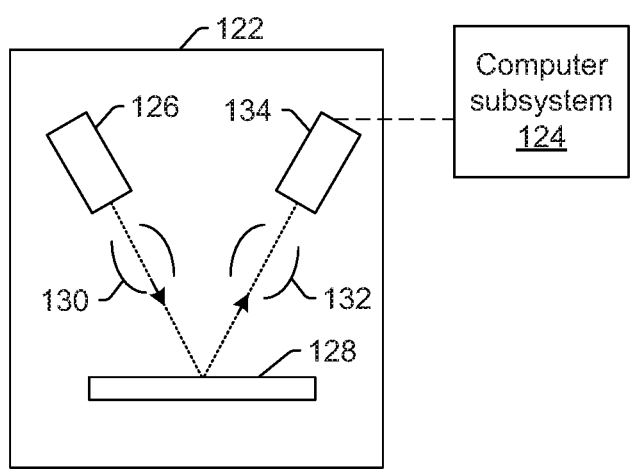

Although the imaging system is described above as being an optical or light-based imaging system, the imaging system may be an electron beam based imaging system. In this manner, in some embodiments, the image input to the two or more encoder layers described herein is generated by an electron beam based imaging system. In one such embodiment shown in FIG. 1a, the imaging system includes electron column 122 coupled to computer subsystem 124. As also shown in FIG. 1a, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a bean current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1a as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam based imaging system may be configured to use multiple modes to generate images of the specimen as described further herein (e.g., with different illumination angles, collection angles, etc.). The multiple modes of the electron beam based imaging system may be different in any image generation parameters of the imaging system.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform one or more functions described further herein for the specimen using output generated by detector 134. Computer subsystem 124 may be configured to perform any additional step(s) described herein. A system that includes the imaging system shown in FIG. 1a may be further configured as described herein.

It is noted that FIG. 1a is provided herein to generally illustrate a configuration of an electron beam based imaging system that may be included in the embodiments described herein. As with the optical based imaging system described above, the electron beam based imaging system configuration described herein may be altered to optimize the performance of the imaging system as is normally performed when designing a commercial imaging system. In addition, the systems described herein may be implemented using an existing system (e.g., by adding functionality described herein to an existing system) such as the eSxxx and eDR-xxxx series of tools that are commercially available from KLA-Tencor. For some such systems, the embodiments described herein may be provided as optional functionality of the system (e.g., in addition to other functionality of the system). Alternatively, the system described herein may be designed "from scratch" to provide a completely new system.

Although the imaging system is described above as being an optical based or electron beam based imaging system, the imaging system may be an ion beam based imaging system. Such an imaging system may be configured as shown in FIG. 1a except that the electron beam source may be replaced with any suitable ion beam source known in the art. In addition, the imaging system may be any other suitable ion beam based imaging system such as those included in commercially available focused ion beam (FIB) systems, helium ion microscopy (HIM) systems, and secondary ion mass spectroscopy (SIMS) systems.

As noted above, the imaging system is configured for scanning energy (e.g., light or electrons) over a physical version of the specimen thereby generating actual images for the physical version of the specimen. In this manner, the imaging system may be configured as an "actual" system, rather than a "virtual" system. For example, a storage medium (not shown) and computer subsystem(s) 102 shown in FIG. 1 may be configured as a "virtual" system. In particular, the storage medium and the computer subsystem(s) are not part of imaging system 10 and do not have any capability for handling the physical version of the specimen. In other words, in systems configured as virtual systems, the output of its one or more "detectors" may be output that was previously generated by one or more detectors of an actual system and that is stored in the virtual system, and during the "scanning," the virtual system may replay the stored output as though the specimen is being scanned. In this manner, scanning the specimen with a virtual system may appear to be the same as though a physical specimen is being scanned with an actual system, while, in reality, the "scanning" involves simply replaying output for the specimen in the same manner as the specimen may be scanned. Systems and methods configured as "virtual" inspection systems are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents. In addition, configuring the one or more virtual systems as a central compute and storage (CCS) system may be performed as described in the above-referenced patent to Duffy. The persistent storage mechanisms described herein can have distributed computing and storage such as the CCS architecture, but the embodiments described herein are not limited to that architecture.

As further noted above, the imaging system may be configured to generate images of the specimen with multiple modes. In general, a "mode" can be defined by the values of parameters of the imaging system used for generating images of a specimen or the output used to generate images of the specimen. Therefore, modes that are different may be different in the values for at least one of the imaging parameters of the imaging system. For example, in one embodiment of an optical based imaging system, at least one of the multiple modes uses at least one wavelength of light for illumination that is different from at least one wavelength of the light for illumination used for at least one other of the multiple modes. The modes may be different in the illumination wavelength is as described further herein (e.g., by using different light sources, different spectral filters, etc.) for different modes. In another embodiment, at least one of the multiple modes uses an illumination channel of the imaging system that is different from an illumination channel of the imaging system used for at least one other of the multiple modes. For example, as noted above, the imaging system may include more than one illumination channel. As such, different illumination channels may be used for different modes.

In one embodiment, the imaging system is an inspection system. For example, the optical and electron beam imaging systems described herein may be configured as inspection systems. In this manner, the image input to the two or more encoder layers is generated by an inspection system in some embodiments. In another embodiment, the imaging system is a defect review system. For example, the optical and electron beam imaging systems described herein may be configured as defect review systems. In a further embodiment, the imaging system is a metrology system. For example, the optical and electron beam imaging systems described herein may be configured as metrology systems. In this manner, the input image to the two or more encoder layers is generated by a metrology system in some embodiments. In particular, the embodiments of the imaging systems described herein and shown in FIGS. 1 and 1a may be modified in one or more parameters to provide different imaging capability depending on the application for which they will be used. In one such example, the imaging system shown in FIG. 1 may be configured to have a higher resolution if it is to be used for defect review or metrology rather than for inspection. In other words, the embodiments of the imaging system shown in FIGS. 1 and 1a describe some general and various configurations for an imaging system that can be tailored in a number of manners that will be obvious to one skilled in the art to produce imaging systems having different imaging capabilities that are more or less suitable for different applications.

The one or more computer subsystems may be configured for acquiring the image for the specimen generated by an imaging subsystem described herein. Acquiring the image may be performed using one of the imaging systems described herein (e.g., by directing light or an electron beam to the specimen and detecting light or an electron beam from the specimen). In this manner, acquiring the image may be performed using the physical specimen itself and some sort of imaging hardware. However, acquiring the image does not necessarily include imaging the specimen using imaging hardware. For example, another system and/or method may generate the image and may store the generated image in one or more storage media such as a virtual inspection system as described herein or another storage media described herein. Therefore, acquiring the image may include acquiring the image from the storage media in which it has been stored.

The component(s), e.g., component(s) 100 shown in FIG. 1, executed by the computer subsystem(s), e.g., computer subsystem 36 and/or computer subsystem(s) 102, include neural network 104. The neural network includes two or more encoder layers configured for determining features of an image for a specimen. The term "encoder" generally refers to a neural network or part of a neural network that "encodes" the information content of input data to a more compact representation. The encode process may be effectively lossy or lossless. In addition, the encode process may or may not be human interpretable. The encoded representation can be a vector of scalar values or distributions.

The neural network also includes two or more decoder layers configured for generating one or more simulated images from the determined features. The term "decoder" refers to a neural network or the part of a neural network that "decodes" the encoded compact representation to possibly the original input and/or a joint representation of the input. The embodiments described herein are generally applicable to encoder-decoder type neural networks, especially deep generative models, which may be configured as described further herein.

In one embodiment, the neural network is a deep learning model. Generally speaking, "deep learning" (also known as deep structured learning, hierarchical learning or deep machine learning) is a branch of machine learning based on a set of algorithms that attempt to model high level abstractions in data. In a simple case, there may be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Some representations are better than others at simplifying the learning task (e.g., face recognition or facial expression recognition). One of the promises of deep learning is replacing handcrafted features with efficient algorithms for unsupervised or semi-supervised feature learning and hierarchical feature extraction.

Research in this area attempts to make better representations and create models to learn these representations from large-scale unlabeled data. Some of the representations are inspired by advances in neuroscience and are loosely based on interpretation of information processing and communication patterns in a nervous system, such as neural coding which attempts to define a relationship between various stimuli and associated neuronal responses in the brain.

Various deep learning architectures such as deep neural networks, convolutional deep neural networks, deep belief networks and recurrent neural networks have been applied to fields like computer vision, automatic speech recognition, natural language processing, audio recognition and bioinformatics where they have been shown to produce state-of-the-art results on various tasks.

In another embodiment, the neural network is a machine learning model. Machine learning can be generally defined as a type of artificial intelligence (AI) that provides computers with the ability to leant without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data—such algorithms overcome following strictly static program instructions by making data driven predictions or decisions, through building a model from sample inputs.

The machine learning described herein may be further performed as described in "Introduction to Statistical Machine Learning," by Sugiyama, Morgan Kaufmann, 2016, 534 pages; "Discriminative, Generative, and imitative Learning," Jebara, MIT Thesis, 2002, 212 pages; and "Principles of Data Mining (Adaptive Computation and Machine Learning)," Hand et al., MIT Press, 2001, 578 pages; which are incorporated by reference as if fully set forth herein. The embodiments described herein may be further configured as described in these references.

In some embodiments, the neural network is a generative model. A "generative" model can be generally defined as a model that is probabilistic in nature. In other words, a "generative" model is not one that performs forward simulation or rule-based approaches and, as such, a model of the physics of the processes involved in generating an actual image (for which a simulated image is being generated) is not necessary. Instead, as described further herein, the generative model can be learned (in that its parameters can be learned) based on a suitable training set of data.

In one embodiment, the neural network is configured as a deep generative model. For example, the model may be configured to have a deep learning architecture in that the model may include multiple layers, which perform a number of algorithms or transformations. The number of layers on one or both sides of the model may vary from that shown in the drawings described herein. For example, the number of layers on the encoder side of the generative model is use case dependent. In addition, the number of layers on the decoder side is use case dependent and may be dependent on the number of layers on the encoder side. In general, the number of layers on one or both sides of the generative model is not significant and is use case dependent. For practical purposes, a suitable range of layers on both sides is from 2 layers to a few tens of layers.

In a further embodiment, the neural network may be a deep neural network with a set of weights that model the world according to the data that it has been fed to train it. Neural networks can be generally defined as a computational approach which is based on a relatively large collection of neural units loosely modeling the way a biological brain solves problems with relatively large clusters of biological neurons connected by axons. Each neural unit is connected with many others, and links can be enforcing or inhibitory in their effect on the activation state of connected neural units. These systems are self-learning and trained rather than explicitly programmed and excel in areas where the solution or feature detection is difficult to express in a traditional computer program.

Neural networks typically consist of multiple layers, and the signal path traverses from front to back. The goal of the neural network is to solve problems in the same way that the human brain would, although several neural networks are much more abstract. Modern neural network projects typically work with a few thousand to a few million neural units and millions of connections. The neural network may have any suitable architecture and/or configuration known in the art.

In another embodiment, the neural network is a convolution neural network (CNN). For example, the embodiments described herein can take advantage of deep learning concepts such as a CNN to solve the normally intractable representation conversion problem (e.g., rendering). The model may have any CNN configuration or architecture known in the art. In another embodiment, the neural network is configured as a fully convolutional model. In additional embodiments, the neural network may be configured as a deep generative model, a CNN, a generative adversarial net (GAN), a conditional generative adversarial net (cGAN), a GAN and a variational autoencoder (VAE), and a network that contains a CNN as a part (i.e., a part of the neural network is configured as a CNN), all of which can be configured as described herein such that the neural network can have arbitrary sized input.

A GAN included in the embodiments described herein may be configured as described in "Generative Adversarial Nets," Goodfellow et al., arXiv:1406.2661, Jun. 10, 2014, 9 pages, which is incorporated by reference as if fully set forth herein. Goodfellow et al. describe a new framework for estimating generative models via an adversarial process, in which two models are simultaneously trained: a generative model G that captures the data distribution, and a discriminative model D that estimates the probability that a sample came from the training data rather than G. The training procedure for G is to maximize the probability of D making a mistake. This framework corresponds to a minimax two-player game. In the space of arbitrary functions G and D, a unique solution exists, with G recovering the training data distribution and D equal to $\frac{1}{2}$ everywhere. In the case where G and D are defined by multilayer perceptrons, the entire system can be trained with backpropagation. There is no need for any Markov chains or unrolled approximate inference networks during either training or generation of samples. Experiments demonstrate the potential of the framework through qualitative and quantitative evaluation of the generated samples. The neural networks of the embodiments described herein may be further configured as described by Goodfellow et al.

A CGAN included in the embodiments described herein may be configured as described in "Conditional Generative Adversarial Nets," by Mirza et al., arXiv:1411.1784, Nov. 6, 2014, 7 pages, which is incorporated by reference as if fully set forth herein. Generative adversarial nets can be extended to a conditional model if both the generator and discriminator are conditioned on some extra information y. y could be any kind of auxiliary information such as class labels or data from other modalities. Conditioning can be performed by feeding y into both the discriminator and generator as an additional input layer. In the generator, the prior input noise $p_z(Z)$, and y are combined in joint hidden representation and the adversarial training framework allows for considerable flexibility in how this hidden representation is composed. In the discriminator x and y are presented as inputs to a discriminative function (embodied in some cases by a multi-layer perceptron (MLP)). The objective function of a two-player minimax game would then be:

$$\min_G \max_D V(D, G) = E_{x \sim p_{data}(x)}[\log D(x|y)] + E_{z \sim p_z(z)}[\log(1 - D(G(z|y)))].$$

The neural networks included in the embodiments described herein may be further configured as described in the above incorporated reference by Mirza et al.

A variational auto-encoder is a component that takes the merits of deep learning and variational inference and leads to significant advances in generative modeling. In addition or alternatively, a variational autoencoder (VAE) combined with a GAN or a deep generative adversarial network (DGAN)) may be configured as described in "Adversarial Autoencoders," Makhzani et al., arXiv:1511.05644v2, May 25, 2016, 16 pages, which is incorporated by reference as if fully set forth herein. The embodiments described herein may be further configured as described in this reference.

The neural network does not include a fully connected layer thereby eliminating constraints on size of the image input to the two or more encoder layers. For example, instead of using fully connected layer(s) as might be done in currently used methods and systems, the neural networks described herein eliminate the fully connected layer(s), which may be replaced by one or more convolutional layers as described further herein. By replacing the fully connected layer(s) with convolutional layer(s), the neural network becomes independent of input image size, meaning that the neural network does not have an upper limit on the input image size like currently used neural networks.

Replacing the fully connected layer(s) with convolutional layer(s) may be done under the following conditions. Given a fully connected layer takes 2-dimensional (N, D) input data, where N is batch size and D is number of channels of input. Often, a reshaping layer is performed before the fully connected layer to transform a 4-dimensional input (N, C, H, W) to 2-dimensional input (N, D) satisfying D=C*H*W, where C is number of channels, H is height, and W is width. Assuming the fully connected layer has O output channels, i.e. the output data dimension from the fully connected layer will be (N, O), the reshaping layer and fully connected layer can be replaced with a convolutional layer with VALID padding with kernel size of (C, O, H, W), and the resulting network can perform exact math on the arbitrary sized input.

In one embodiment, the one or more computer subsystems, the one or more components, and the neural network do not crop the image input to the two or more encoder layers. In another embodiment, the one or more computer subsystems, the one or more components, and the neural network do not reconstruct the one or more simulated images from two or more cropped images. Therefore, the embodiments described herein are different than currently used methods in a number of different ways.

Figure 2:
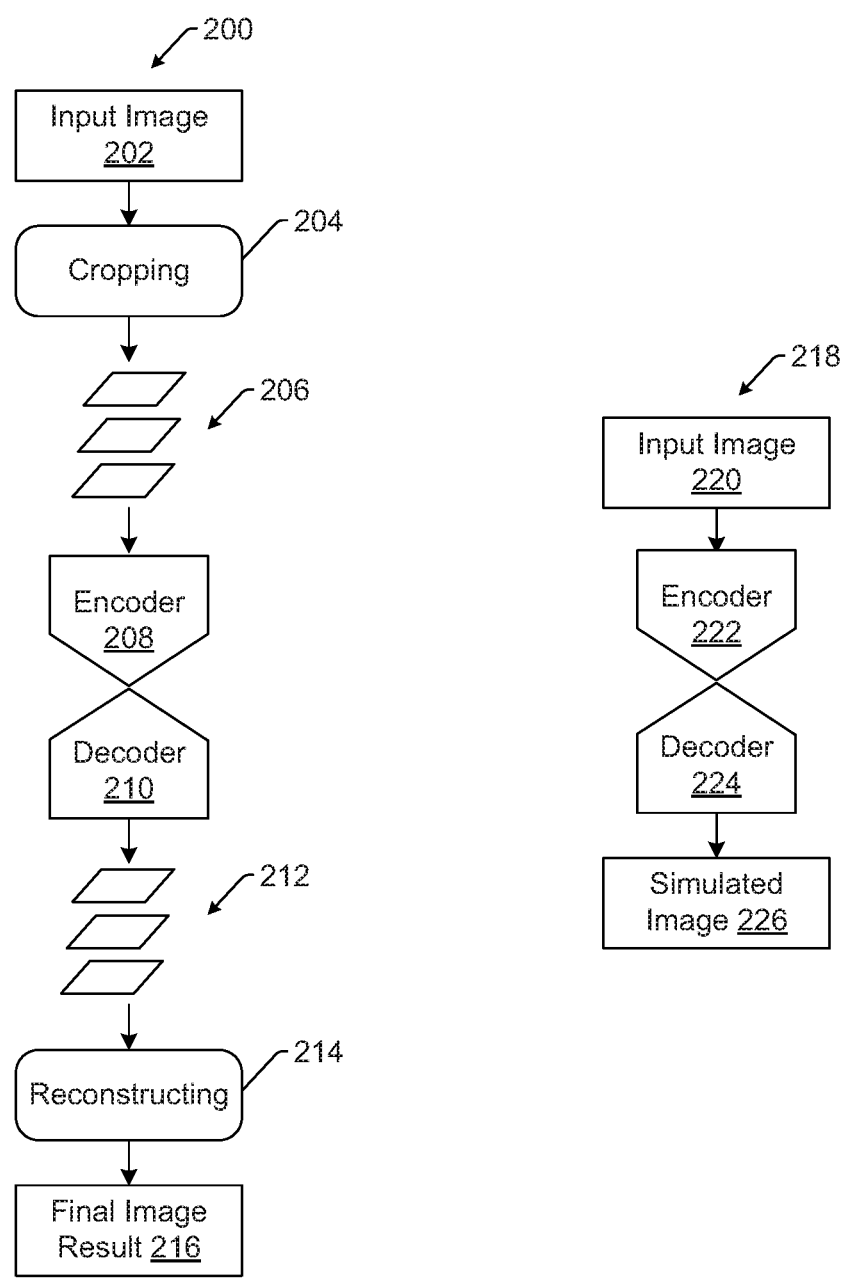
FIG. 2 is a schematic diagram illustrating one example of a currently used method for generating a simulated image from an input image and one embodiment of generating a simulated image from an input image without the cropping and reconstructing steps of the currently used method.

As shown in FIG. 2, for example, currently used method 200 may take input image 202 that has a size of 1024 pixels by 1024 pixels. The method may include cropping 204 that generates set 206 of patch images from input image 202, where each of the patch images has a size that is significantly smaller than the input image and is the largest size that can be processed by the method. For example, cropping 204 may generate set 206 of 923,521 patch images, each having a size of 64 pixels by 64 pixels. Those patch images may be input to a neural network that includes encoder 208 and decoder 210, which may produce a set of results equivalent to the input to the encoder. For example, if the set of patch images described above is input to encoder 208, then decoder 210 will produce set 212 of patch images that includes 923,521 patch images, each having a size of 64 pixels by 64 pixels. The method may then include reconstructing step 214, that uses the set of patch images to generate final image result 216, which has the same size as the input image (i.e., 1024 pixels by 1024 pixels).

In contrast, the embodiments described herein do not perform any cropping on the input image and/or do not generate the input image by any cropping performed on an image that is larger than the input image. In other words, once the input image is input to the methods and systems described herein it is not cropped. In addition, the input image used in the embodiments described herein is not cropped out of a larger image. The embodiments described herein also do not perform any reconstructing of the final image from any smaller images generated by any of the elements of the embodiments described herein. For example, as shown in FIG. 2, one embodiment 218 may take input image 220 as input to a neural network that includes encoder 222 and decoder 224. Encoder 222 may include two or more encoder layers, which may be configured according to any of the embodiments described herein. In addition, decoder 224 may include two or more decoder layers, which may be configured according to any of the embodiments described herein.

In one embodiment, as described further herein, the neural network may be configured as fully convolutional neural network, which refers to the configuration in which each layer type has no assumption on specific input size and the entire network can operate on arbitrarily sized input for both training and inference. In addition, the neural network may be configured as described further herein to perform boundary damping. The decoder may be configured to produce simulated image 226, which has the same image size as the input image. For example, if the input image size is 1024 pixels by 1024 pixels, then the output image size is 1024 pixels by 1024 pixels. Therefore, as shown by comparing currently used method 200 and embodiment 218, the embodiments described herein may not be configured to perform any cropping and reconstructing steps.

In one embodiment, the one or more computer subsystems are configured for setting up the neural network by replacing the fully connected layer in a preexisting neural network with a group of convolutional layers thereby creating the neural network. For example, the embodiments described herein may follow the general idea described in "Fully convolutional networks for semantic segmentation" by Long et al., CVPR2015, pp. 3431-3440, 2015, which is incorporated by reference as if fully set forth herein, to replace a fully connected layer of a neural network by a convolutional layer to make the entire neural network independent on the input size. The embodiments described herein may be further configured as described in this reference.

Figure 3A:
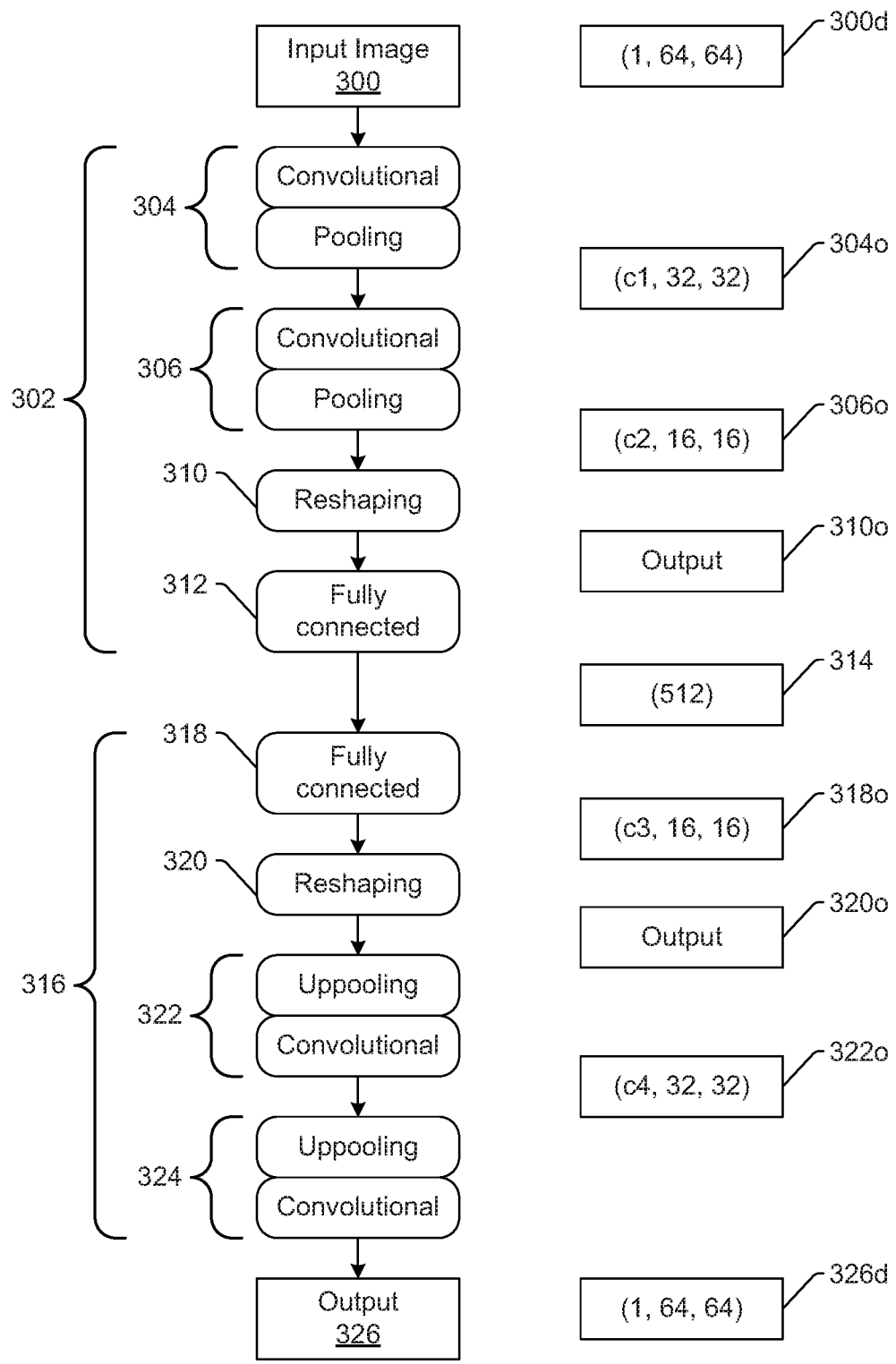
FIG. 3a is a schematic diagram illustrating one example of a currently used neural network having a fixed input image size.
Figure 3B:
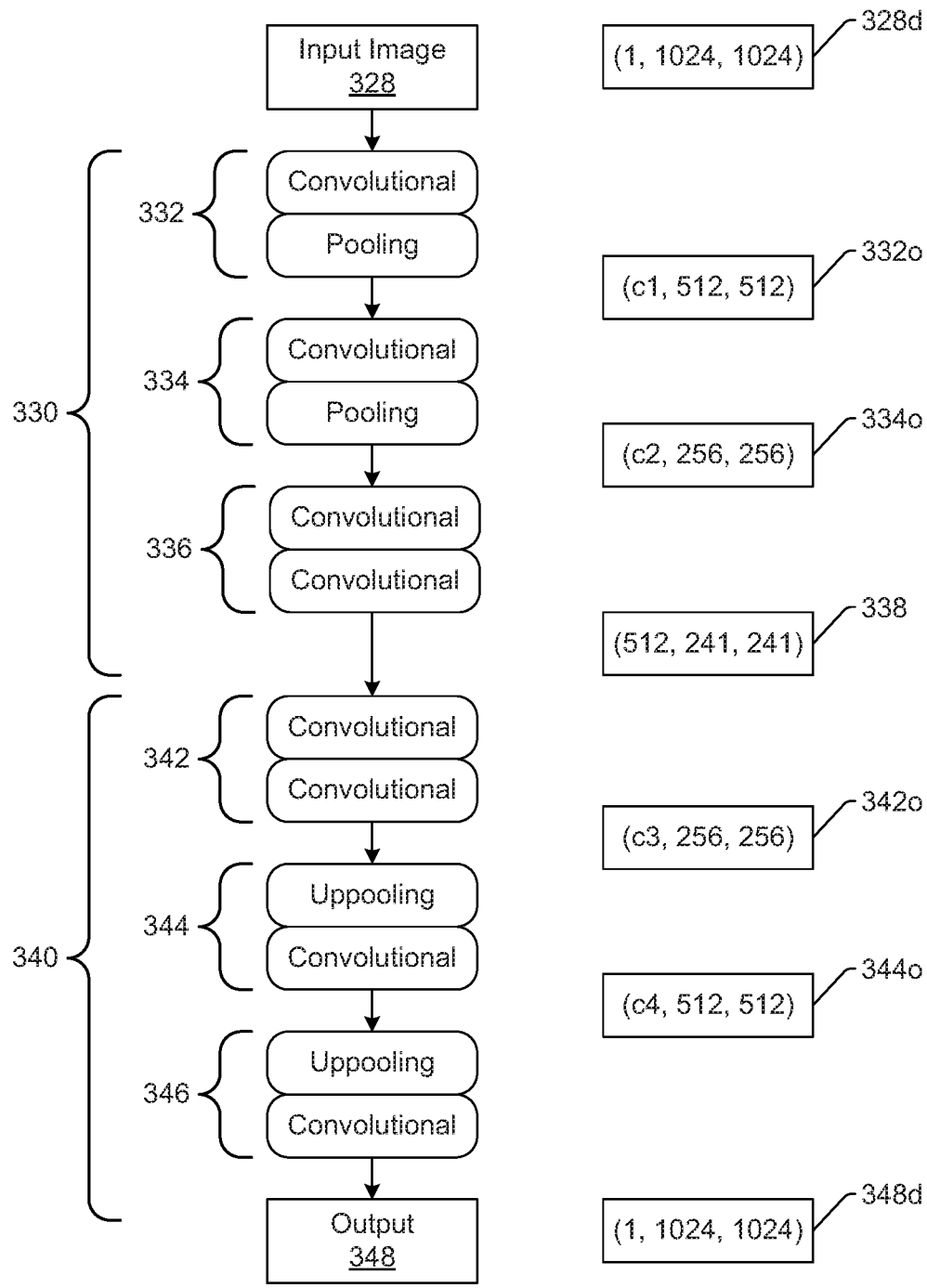
FIG. 3b is a schematic diagram illustrating one embodiment of a neural network that enables arbitrary input image size.

FIGS. 3a and 3b illustrate how a currently used encoder-decoder network with fixed input size (i.e., 64 pixels by 64 pixels) may be converted to a fully convolutional network that enables arbitrary input size. In particular, FIG. 3a shows a currently used neural network with a fixed input size of 64 pixels by 64 pixels, and FIG. 3b shows one embodiment of a neural network that enables arbitrary input size with the approaches described herein. In FIGS. 3a and 3b, the input and output dimensions are shown at a few stages, and in each such instance, the dimensions have the format of (C, H, W), where C is the number of channels, H is the height of the input or output, and W is the width of the input or output.

As shown in FIG. 3a, input image 300 may be input to encoder portion 302 of the currently used network. Input dimensions 300d of the input image are (1, 64, 64). Encoder portion 302 includes two sets 304 and 306 of convolutional and pooling layers, reshaping layer 310, and fully connected layer 312. The input image is input to set 304 of convolutional and pooling layers, which generates output 304o (c1, 32, 32) that is input to set 306 of convolutional and pooling layers. Output 306o (c2, 16, 16) of set 306 is input to reshaping layer 310, which generates output 310o, which is input to fully connected layer 312, which generates representation 314 (512), that is input to the decoder portion of the currently used network.

Decoder portion 316 of the currently used network includes fully connected layer 318, reshaping layer 320, and sets 322 and 324 of convolutional and uppooling layers. Representation 314 is input to fully connected layer 318, which produces output 318o (c3, 16, 16). Output 318o is input to reshaping layer 320, which produces output 320o, which is input to set 322 of convolutional and uppooling layers, which produces output 322o (c4, 32, 32). Output 322o is input to set 324 of convolutional and uppooling layers that produces output 326, which has output dimensions 326d (1, 64, 64), and which is the output of the neural network.

In contrast, as shown in FIG. 3b, input image 328 is input to encoder portion 330 of a neural network configured according to embodiments described herein. Input image 328 has input dimensions 328d of (1, 1024, 1024). Encoder portion 330 includes sets 332 and 334 of convolutional and pooling layers and set 336 of convolutional layers. Input image 328 is input to set 332 of convolutional and pooling layers that produces output 332o (c1, 512, 512), which is input to set 334 of convolutional and pooling layers that produces output 334o (c2, 256, 256). Output 334o is input, to set 336 of convolutional layers, which produces representation 338 (512, 241, 241).

Representation 338 is input to decoder portion 340 of the neural network embodiment. Decoder portion 340 includes set 342 of convolutional layers and sets 344 and 346 of convolutional and uppooling layers. Representation 338 is input to set 342 of convolutional layers, which produces output 342o (c3, 256, 256). Output 342o is input to set 344 of convolutional and uppooling layers, which produces output 344o (c4, 512, 512). Output 344o is input to set 346 of convolutional and uppooling layers, which produces output 348, which has output dimensions 348d of (1, 1024, 1024), and which is the output of the neural network.

Unlike the methods and systems described by Long et al. in the reference incorporated above, the replacement of the fully connected layer with convolutional layers as described herein is not constrained to one-to-one mapping of fully connected and convolutional layers. In the context of the embodiments described herein, "one-to-one mapping" would involve replacing one fully connected layer (or one fully connected layer+one reshaping layer) with one convolutional layer. However, such a configuration may lead to substantially large kernel size for resulting convolutional layers. For example, (following the same notations as above) if the input dimensions to a reshaping layer are (N, 64, 32, 32), the output of the reshaping layer (i.e., the input to the fully connected layer) is (N, 64*32*32), assuming the output of the fully connected layer is (N, 256), the reshaping and fully connected layers can be replaced by a convolutional layer with kernel size (64, 256, 32, 32).

Since the H and W (i.e., 32) in kernel (64, 256, 32, 32) are substantially large compared to practical choices (e.g., 3 or 5 or 7 or less than 10), the learning process can be inefficient. Therefore, the convolutional layer with a relatively large kernel can be approximated by a group of convolutional layers with relatively small kernels. For example, in the example provided above, (64, 256, 32, 32) can be replaced by (64, M, 32, 1) and (M, 256, 1, 32) where M is a free hyper parameter.

Such group replacement may be required such that the output dimension of applying the group of convolutional layers is the same as the output dimension of applying the original convolutional layers with kernel (C, O, H, W). The common choice of the group of convolutional layers can be (C, O, H, W)==>(C, M, H, k)+(M, O, k, W) or (C, M, k, H)+(M, O, W, k), where k and M are hyper parameters and k is often substantially small (e.g., 1, 2, 3, . . . ) and much smaller than H or W.

When the window size of the fully connected layer is large enough so as to take account of the semiconductor process conditions (e.g., point spread function of lithography tool and/or optical inspection tool, or the chemical and physical reaction in etching process, etc.), the fully connected layer may be replaced with a group of convolutional layers (each with a smaller filter window size (in H and W)) as described herein, and the effective window size of the entire group is identical to or larger than the size in the fully connected layer. This approach removes the input size constraint and also reduces the total number of parameters (for both training and runtime). In this manner, the embodiments described herein may use a group of convolutional layers to reduce the model size while satisfying the window size due to semiconductor processes.

In some embodiments, the image input to the two or more encoder layers is an entire frame image generated for the specimen. The term "frame" image is generally defined herein as data or an image for a portion of a die in a swath of data or images acquired during scanning of a specimen such as a wafer or reticle. A "frame" or "job" may also be generally defined as a relatively small portion of all of the output generated by an imaging subsystem that can be collectively processed as a unit by the system. Therefore, a "frame" of output can vary depending on the imaging subsystem configuration as well as the configuration of any components included in the system for handling and/or processing the output generated by the imaging subsystem. However, an image frame will generally be substantially larger than a patch image and the maximum image size that can typically be input to currently used neural networks for simulating an image. For example, an image frame for the embodiments described herein may be 1024 pixels by 1024 pixels or 512 pixels by 512 pixels while a patch image may have a typical size of 64 pixels by 64 pixels or 32 pixels by 32 pixels.

In another embodiment, the image input to the two or more encoder layers is an entire die image for the specimen. For example, the entire die image may include all of the image data or output generated for a die on a specimen by an imaging system. In this manner, unlike currently used neural networks, the embodiments described herein enable entire frame or entire die rendering in practice. In particular, the embodiments described herein replace fully connected layer(s) with convolutional layer(s) for neural networks thereby enabling arbitrary image size. In this manner, the embodiments described herein enable entire frame and die runtime estimation for neural network use cases.

The embodiments described herein have, therefore, a number of advantages over other methods and systems for generating simulating images. For example, the embodiments described herein enable arbitrary input size for training and runtime. In addition, the embodiments described herein enormously reduce the runtime computation by 100× to 1000× compared to currently used methods and systems. Therefore, the embodiments described herein reduce the runtime hardware cost compared to currently used methods and systems. In addition, the embodiments enable entire frame and die estimation. Furthermore, the embodiments described herein advantageously reduce the model size (i.e., the number of model parameters) while keeping the same operating window size. In this manner, the embodiments described herein reduce the communication overload in the training process. Moreover, no alternative method has equivalent performance to the embodiments described herein.

The embodiments described herein may or may not be configured for training the neural network. For example, another method and/or system may be configured to generate a trained neural network, which can then be accessed and used by the embodiments described herein.

In one embodiment, the one or more computer subsystems are configured for training the neural network using a fovy-decay weighted loss function to alter boundary effects. For example, depending on the encoder and decoder topology and convolutional type (e.g., valid, full, same) in encoder and decoder, the boundary part of the output may undergo different mathematical operations compared to the center part of the output, due to the boundary effect of the convolutional layer, especially when the neural network is relatively deep and the training image is relatively small. In particular, convolutional layers have three padding types: VALID, SAME, and FULL. If the input image size is (H, W) and convolutional filter size is (h, w), the output size from (a) VALID is (H−h+1, W−w+1), (b) SAME is (H, w), and (c) FULL is (H+h−1, W+w−1). If SAME or FULL padding is used, at the boundary part of the input image, the convolutional filter will be placed outside of the image, which is equivalent to considering the pixels outside of the input image as zero valued. This means the convolutional result at the boundary of an image is often not representative, and artifact results can show at the boundary.

To remove the boundary region contribution, a fovy-decay weighted loss function may be used during the training process, where "fovy" is commonly used (as in graphics applications such as OpenGL) to refer to the field of view in the y direction. For example, when training a fully convolutional network with SAME or FULL padding, the training will take into account the results at boundary pixels, and this introduces a lot of noise from artifacts to the learning process. To address this issue, a fovy-decay weighted loss function may be introduced, for example, a 3×3 fovy,
0.5, 0.6, 0.5,
0.6, 1.0, 0.6,
0.5, 0.6, 0.5
in which the center regions have a weight closer or equal to 1.0 and near boundary region the value is less than 1.0. The motivation of fovy-decay weighted loss is to make the learning process focus on the relatively center region pixels.

The shape of the decay can be circular, square, or rectangular depending on the encoder and decoder topology and the related application. In addition, common ways to generate fovy-decay weights can be: (1) assigning a fixed relatively small value to a constant border, and 1.0 of left center region; (2) 2D Gaussian kernel with properly chosen mean and standard deviation; and (3) two 1D Gaussian kernels with properly chosen mean and standard deviation. For some applications, this step may be omitted. In this manner, the embodiments described herein can use the fovy-decay weighted loss function to remove the undesired boundary effect (or boundary noise) training.

In general, training the neural network may include acquiring data (e.g., both input images and simulated images, which may include any of the input and simulated images described herein). In one embodiment, the one or more computer subsystems are configured for training the neural network using a batch of training images, each having the same arbitrary size. In an additional embodiment, the one or more computer subsystems are configured for training the neural network using a batch of training images, and two or more of the training images in the batch have different arbitrary sizes. In this manner, the batch of arbitrarily sized images may include multiple sized images or each batch may include images all of the same arbitrary size. In practice, for computational and implementation efficiency, each batch may include images all of the same arbitrary size.

The images that are used to train the neural network may or may not have the same size as the input image. For example, the input image may have a minimal size requirement due to the network topology, and no minimum size limit as long as it can fit the hardware storage limit. The minimal size may be determined by the network topology and is often chosen to reflect the optical setup. In practice, the patch image is often larger than the minimal size requirement. In practice, we can: (1) train on patch images and predict on patch or frame images; or (2) train on frame images and predict on patch or frame images.

In some such embodiments, given a set of arbitrarily sized training images (each of them may be no less than the designed minimum size, i.e., 64 pixels by 64 pixels in the example shown in FIG. 3a), at the training step, a random batch of images are selected. The training may be performed in one step, with no sub-steps. In addition, there are no extra steps required to prepare the training data. In theory, the batch of arbitrarily sized images may be used for training. However, to take advantage of hardware low level instructions, a batch of fixed sized patches may be randomly sampled out from the selected images. These sampled patch images may be used for the training step. The patch size can be different at the training step although in common cases it is predetermined. Then at runtime, given a set of arbitrarily sized runtime images, each of them may be fed to the network to generate the prediction (i.e., simulated image(s)) without any cropping or reconstruction steps.

Training the model may be further performed as described in U.S. patent application Ser. No. 15/176,139 by Zhang et al. filed Jun. 7, 2016, and Ser. No. 15/394,790 by Bhaskar et al. filed Dec. 29, 2016, which are incorporated by reference as if fully set forth herein. The embodiments described herein may be further configured as described in these patent applications.

The features determined by the encoder layers may include any suitable features known in the art that can be inferred from the input and used to generate the output described further herein. For example, the features may include a vector of intensity values per pixel. The features may also include any other types of features described herein, e.g., vectors of scalar values, vectors of independent distributions, joint distributions, or any other suitable feature types known in the art.

Each of the layers of the neural network described above may have one or more parameters such as weights, W, and biases, B, whose values can be determined by training the neural network, which may be performed as described further herein. For example, the weights and biases of any layers included in the neural network may be determined during training by minimizing a cost function. The cost function may vary depending on the transformation that is being performed on the images.

The neural network described herein may be generated for specific specimens (e.g., specific wafers or reticles), processes, and imaging parameters. In other words, the neural network described herein may be specimen specific, process specific, and imaging parameter specific. For example, in one embodiment, each neural network may be trained to be specific to a particular design and wafer layer. The trained neural network will then only be used to perform predictions for that layer. In this manner, different neural networks may be generated for different wafer layers. However, in another embodiment, a single neural network may be trained with data from different designs and wafer type layers. The resulting neural network may be used to perform predictions in general for all types of the specimens included in the training data. In addition, different neural networks may be generated for different sets of imaging parameters (e.g., different imaging modes) used to generate the input image(s), and possibly for different sets of imaging parameters (e.g., different imaging modes) of simulated images for which the transformations are performed (e.g., in the case of generating multiple simulated images corresponding to different imaging modes). In general, a neural network may be independent of tool as long as the selected imaging modes are repeatable across the tools. Each of the different neural networks may be generated with different training sets of data. Each of the different training sets of data may be generated in any suitable manner.

The embodiments described herein may be configured for performing a number of different types of transformations (i.e., transforming the input image to the one or more simulated images). For example, in some embodiments, the neural network may be configured to generate one or more high resolution images from a low resolution input image. The term "low resolution image" of a specimen, as used herein, is generally defined as an image in which all of the patterned features formed in the area of the specimen at which the image was generated are not resolved in the image. For example, some of the patterned features in the area of the specimen at which a low resolution image was generated may be resolved in the low resolution image if their size is large enough to render them resolvable. However, the low resolution image is not generated at a resolution that renders all patterned features in the image resolvable. In this manner, a "low resolution image," as that term is used herein, does not contain information about patterned features on the specimen that is sufficient for the low resolution image to be used for applications such as defect review, which may include defect classification and/or verification, and metrology. In addition, a "low resolution image" as that term is used herein generally refers to images generated by inspection systems, which typically have relatively lower resolution (e.g., lower than defect review and/or metrology systems) in order to have relatively fast throughput.

The "low resolution images" may also be "low resolution" in that they have a lower resolution than a "high resolution image" described herein. A "high resolution image" as that term is used herein can be generally defined as an image in which all patterned features of the specimen are resolved with relatively high accuracy. In this manner, all of the patterned features in the area of the specimen for which a high resolution image is generated are resolved in the high resolution image regardless of their size. As such, a "high resolution image," as that term is used herein, contains information about patterned features of the specimen that is sufficient for the high resolution image to be used for applications such as defect review, which may include defect classification and/or verification, and metrology. In addition, a "high resolution image" as that term is used herein generally refers to images that cannot be generated by inspection systems during routine operation, which are configured to sacrifice resolution capability for increased throughput.

Low resolution images may also include, for example, optical images of the specimen, and high resolution images may include electron beam images (e.g., a scanning electron microscope (SEM) image) or design data for the specimen. In addition, as described further herein, a high resolution image for a specimen may be generated with a neural network configured as described herein. Therefore, as described further herein, the embodiments may be configured for performing optical to SEM and/or design data transformation(s) using a deep learning technique.

The embodiments described herein may be configured to perform a number of different functions using the one or more simulated images, possibly in combination with the input image. For example, the one or more computer subsystems may be configured for (a) representation learning of IC structures on optical, electron beam, and mask tools; (b) defect detection and classification; and (c) entire frame or die inspection. Each of these functions may be performed as described further herein.

In one embodiment, the one or more computer subsystems are configured for classifying a defect detected in the image input to the two or more encoder layers or the one or more simulated images, and the classifying is performed based on the one or more simulated images. For example, the input image to the neural network may be an optical image of a specimen and the one or more simulated images generated by the neural network may include a higher resolution image of the specimen such as an image that may be generated by an electron beam imaging subsystem and/or an image of design data or design information for the specimen.

One benefit of optical image to SEM and/or design transformations is that optical inspection is still the key for high volume production yield in semiconductor manufacturing processes. Due to lack of resolution, defects detected by optical inspectors require SEM review for defect classification. Methods that automatically transform optical to SEM and/or design can potentially reduce SEM review requirements for yield management, thereby reducing total inspection cycle time. For example, the embodiments described herein can eliminate the need for acquiring SEM images on a defect review system after specimen inspection since the simulated image(s) described herein can be 1)

acquired without the specimen and without imaging hardware and 2) used for defect review applications such as defect classification.

The defect that is classified by the neural network may be detected in the input image and/or the one or more simulated images described herein. In addition, classifying the defect based on the one or more simulated images may be performed in any suitable manner known in the art. For example, the one or more simulated images may be used as input to any suitable defect classification methods and/or algorithms known in the art. In other words, the one or more simulated images may be used as any other images for defect classification. Results of the defect classification performed by the embodiments described herein may have any suitable format (e.g., defect classification codes, etc.).

In a further embodiment, the one or more computer subsystems are configured for detecting a defect on the specimen based on the one or more simulated images. The computer subsystem(s) may be configured to use the one or more simulated images to detect defects on the specimen in any suitable manner. For example, the computer subsystem(s) may be configured to apply one or more defect detection algorithms and/or methods to the one or more simulated images, which may include any suitable defect detection algorithms and/or methods known in the art. In one such example, the computer subsystem(s) may be configured to compare the one or more simulated images to a reference for the specimen and then apply a threshold to results of the comparison. Pixels in the simulated image(s) having results of the comparison above the threshold may be identified as defects while pixels in the simulated image(s) having results of the comparison below the threshold may not be identified as defects.

In another example, the computer subsystem(s) may be configured for single image detection as described in U.S. patent application Ser. No. 15/353,210 filed Nov. 16, 2016 by Karsenti et al., which is incorporated by reference as if fully set forth herein. In one such embodiment, as described in this patent application, the features determined for the input image by the neural network may be used to detect defects in the input image. For example, the computer subsystem(s) may be configured for selecting labels for pixels or block of pixels in the input image based on (1) the determined features and (2) mapping of the pixels or blocks of the pixels of an input feature map volume into the labels. The computer subsystems may be further configured for detecting defects on the specimen based on the selected labels for the pixels or blocks.

In addition, the computer subsystem(s) may be configured to detect defects on the specimen using both the image input to the neural network in combination with the one or more simulated images generated by the neural network. For example, if the input image is a low resolution image and the one or more simulated images include a high resolution image, a position of a defect detected in the low resolution image may be identified in the high resolution image to determine the design context of the defect, which can then be used to determine if the defect is a nuisance defect or an actual defect. In addition, a position of a defect detected in the low resolution image may be used to identify the position of the defect in the high resolution image to determine if the defect is present (can be detected) in the high resolution image. If the defect can be detected in the high resolution image, it is designated as an actual defect. If the defect cannot be detected in the high resolution image, it is designated as a nuisance defect.

In an additional embodiment, the one or more computer subsystems are configured for measuring one or more features of the specimen or a defect detected on the specimen based on the one or more simulated images. For example, the neural network may be configured such that the one or more simulated images generated by the neural network are high resolution image(s) generated from an input image that is a low resolution image. The high resolution image(s) may therefore contain greater detail about features formed on the specimen (e.g., patterned features such as lines, spaces, contacts, etc. as well as defects on the specimen) than the input images. The computer subsystems may then use those high resolution image(s) to measure or determine one or more characteristics of the features on the specimen.

The one or more characteristics of the features may be determined in any suitable manner. In addition, the one or more characteristics of the features that are determined or measured by the computer subsystem(s) may include any suitable characteristics such as dimension (e.g., line width, contact diameter, etc.), shape, relative location, etc. The measurements may be performed on the simulated image(s) by the computer subsystem(s) as described in U.S. Patent Application Publication Nos. 2016/0116420 published on Apr. 28, 2016 by Duffy et al., 2016/0372303 published on Dec. 22, 2016 by Park et al., and 2016/0377425 published on Dec. 29, 2016 by Gupta et al., which are incorporated by reference as if fully set forth herein. The embodiments described herein may be further configured as described in these publications.

In some embodiments, the one or more computer subsystems are configured for learning a representation of one or more structures on the specimen by determining values for the features that render the one or more simulated images substantially the same as the image input to the two or more encoder layers. The representation may be defined by all of the features that are determined for an input image. The representation may be learned by attempting to generate one or more simulated images that are substantially equivalent to the input image. For example, the input image may be input to the two or more encoder layers and the neural network may generate the one or more simulated images. Differences between the one or more simulated images and the input image may be determined, and information about those differences may be used to alter one or more parameters of the neural network (such as those described further herein). The neural network with the altered parameters may be used to repeat the process iteratively until the one or more simulated images substantially match the input images (i.e., the differences between the one or more simulated images and the input image have been effectively minimized). Such a learning process may be further performed as described in U.S. patent application Ser. No. 15/176,139 filed on Jun. 7, 2016 by Zhang et al., which is incorporated by reference as if fully set forth herein. The embodiments described herein may be further configured as described in this patent application.

The embodiments described herein may be further configured for performing other transformations (from an input image to a simulated image) such as those described in commonly owned U.S. patent application Ser. No. 15/176, 139 filed Jun. 7, 2016 by Zhang et al., Ser. No. 15/353,210 filed Nov. 16, 2016 by Karsenti et al., Ser. No. 15/394,790 filed Dec. 29, 2016 by Bhaskar et al., Ser. No. 15/394,792 filed Dec. 29, 2016 by Bhaskar et al., Ser. No. 15/396,800 filed Jan. 2, 2017 by Zhang et al., Ser. No. 15/402,094 filed Jan. 9, 2017 by Bhaskar et al., Ser. No. 15/402,169 filed Jan. 9, 2017 by Bhaskar et al., and Ser. No. 15/402,197 filed Jan.

9, 2017 by Park et al., which are incorporated by reference as if fully set forth herein. The embodiments described herein may be further configured as described in these patent applications. In addition, the embodiments described herein may be configured to perform any steps described in these patent applications.

Another embodiment of a system configured to generate a simulated image from an input image includes an imaging subsystem configured for generating an image of a specimen. The imaging subsystem may have any configuration described herein. The system also includes one or more computer subsystems, e.g., computer subsystem(s) 102 shown in FIG. 1, which may be configured as described further herein, and one or more components, e.g., component(s) 100, executed by the one or more computer subsystems, which may include any of the component(s) described herein. The component(s) include a neural network, e.g., neural network 104, which may be configured as described herein. For example, the neural network includes two or more encoder layers configured for determining features of the image and two or more decoder layers configured for generating one or more simulated images from the determined features. The neural network does not include a fully connected layer thereby eliminating constraints on size of the image input to the two or more encoder layers. The neural network may be further configured as described further herein. This system embodiment may be further configured as described herein.

Each of the embodiments of each of the systems described above may be combined together into one single embodiment.

Another embodiment relates to a computer-implemented method for generating a simulated image from an input image. The method includes acquiring an image for a specimen. The method also includes determining features of the image for the specimen by inputting the image into two or more encoder layers of a neural network. In addition, the method includes generating one or more simulated images from the determined features. Generating the one or more simulated images is performed by two or more decoder layers of the neural network. The acquiring, determining, and generating are performed by one or more computer systems. One or more components are executed by the one or more computer systems, and the one or more components include the neural network.

Each of the steps of the method may be performed as described further herein. The method may also include any other step(s) that can be performed by the system, computer subsystem(s), and/or imaging systems or subsystems described herein. The one or more computer systems, the one or more components, and the neural network may be configured according to any of the embodiments described herein, e.g., computer subsystem(s) 102, component(s) 100, and neural network 104. In addition, the method described above may be performed by any of the system embodiments described herein.

Figure 4:
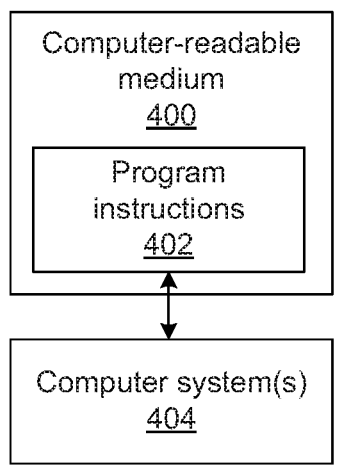
FIG. 4 is a block diagram illustrating one embodiment of a non-transitory computer-readable medium storing program instructions for causing one or more computer systems to perform a computer-implemented method described herein.

An additional embodiment relates to a non-transitory computer-readable medium storing program instructions executable on one or more computer systems for performing a computer-implemented method for generating a simulated image from an input image. One such embodiment is shown in FIG. 4. In particular, as shown in FIG. 4, non-transitory computer-readable medium 400 includes program instructions 402 executable on computer system(s) 404. The computer-implemented method may include any step(s) of any method(s) described herein.

Program instructions 402 implementing methods such as those described herein may be stored on computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system(s) 404 may be configured according to any of the embodiments described herein.

Further modifications and alternative embodiments of various aspects of the invention will be apparent to those skilled in the art in view of this description. For example, methods and systems for generating a simulated image from an input image are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to generate a simulated image from an input image, comprising:
   one or more computer subsystems configured to acquire an image for a specimen by directing energy to the specimen and detecting energy from the specimen using the specimen itself and imaging hardware; and
   one or more components executed by the one or more computer subsystems, wherein the one or more components comprise:
      a neural network, wherein the neural network comprises:
         two or more encoder layers configured for determining features of the image for the specimen, wherein the image is a low resolution image of the specimen; and
         two or more decoder layers configured for generating one or more simulated images from the determined features, wherein the one or more simulated images are one or more high resolution images of the specimen, wherein the neural network is configured as a deep generative model, and wherein the neural network does not comprise a fully connected layer thereby eliminating constraints on size of the image input to the two or more encoders layers.

2. The system of claim 1, wherein the neural network is further configured as a fully convolutional model.

3. The system of claim 1, wherein the neural network is further configured as a generative adversarial net.

4. The system of claim 1, wherein the neural network is further configured as a conditional generative adversarial net.

5. The system of claim 1, wherein the neural network is further configured as a generative adversarial network and variational autoencoder.

6. The system of claim 1, wherein a part of the neural network is further configured as a convolutional neural network.

7. The system of claim 1, wherein the one or more computer subsystems, the one or more components, and the neural network do not crop the image input to the two or more encoder layers.

8. The system of claim 1, wherein the one or more computer subsystems, the one or more components, and the neural network do not reconstruct the one or more simulated images from two or more cropped images.

9. The system of claim 1, wherein the one or more computer subsystems are further configured for setting up the neural network by replacing a fully connected layer in a preexisting neural network with a group of convolutional layers thereby creating the neural network.

10. The system of claim 1, wherein the one or more computer subsystems are configured for training the neural network using a fovy-decay weighted loss function to alter boundary effects.

11. The system of claim 1, wherein the one or more computer subsystems are configured for training the neural network using a hatch of training images, each having the same arbitrary size.

12. The system of claim 1, wherein the one or more computer subsystems are configured for training the neural network using a batch of training images, and wherein two or more of the training images in the batch have different arbitrary sizes.

13. The system of claim 1, wherein the image input to the two or more encoder layers is an entire frame image generated for the specimen.

14. The system of claim 1, wherein the image input to the two or more encoder layers is an entire die image for the specimen.

15. The system of claim 1, wherein the image input to the two or more encoder layers is generated by an electron beam based imaging system.

16. The system of claim 1, wherein the image input to the two or more encoder layers is generated by an optical based imaging system.

17. The system of claim 1, wherein the image input to the two or more encoder layers is generated by an inspection system.

18. The system of claim 1, wherein the image input to the two or more encoder layers is generated by a metrology system.

19. The system of claim 1, wherein the specimen is a wafer.

20. The system of claim 1, wherein the specimen is a reticle.

21. The system of claim 1, wherein the one or more computer subsystems are configured for detecting a defect on the specimen based on the one or more simulated images.

22. The system of claim 1, wherein the one or more computer subsystems are configured for classifying a defect detected in the image input to the two or more encoder layers or the one or more simulated images, and wherein said classifying is performed based on the one or more simulated images.

23. The system of claim 1, wherein the one or more computer subsystems are configured for measuring one or more features of the specimen or a defect detected on the specimen based on the one or more simulated images.

24. The system of claim 1, wherein the one or more computer subsystems are configured for learning a representation of one or more structures on the specimen by determining values for the features that render the one or more simulated images substantially the same as the image input to the two or more encoder layers.

25. A system configured to generate a simulated image from an input image, comprising:
   an imaging subsystem configured for generating an image of a specimen by directing energy to the specimen and detecting energy from the specimen using the specimen itself and imaging hardware, wherein the image is a low resolution image of the specimen;
   one or more computer subsystems configured for acquiring the image; and
   one or more components executed by the one or more computer subsystems, wherein the one or more components comprise:
      a neural network, wherein the neural network comprises:
         two or more encoder layers configured for determining features of the image; and
         two or more decoder layers configured for generating one or more simulated images from the determined features, wherein the one or more simulated images are one or more high resolution images of the specimen, wherein the neural network is configured as a deep generative model, and wherein the neural network does not comprise a fully connected layer thereby eliminating constraints on size of the image input to the two or more encoder layers.

26. A non-transitory computer-readable medium, storing program instructions executable on one or more computer systems for performing a computer-implemented method for generating a simulated image from an input image, wherein the computer-implemented method comprises:
   acquiring an image for a specimen by directing energy to the specimen and detecting energy from the specimen using the specimen itself and imaging hardware;
   determining features of the image for the specimen by inputting the image into two or more encoder layers of a neural network, wherein the image is a low resolution image of the specimen, wherein the neural network is configured as a deep generative model, and wherein the neural network does not comprise a fully connected layer thereby eliminating constraints on size of the image input to the two or more encoder layers; and
   generating one or more simulated images from the determined features, wherein the one or more simulated images are one or more high resolution images of the specimen, wherein generating the one or more simulated images is performed by two or more decoder layers of the neural network, wherein said acquiring, said determining, and said generating are performed by the one or more computer systems, wherein one or more components are executed by the one or more computer systems, and wherein the one or more components comprise the neural network.

27. A computer-implemented method for generating a simulated image from an input image, comprising:
   acquiring an image for a specimen by directing energy to the specimen and detecting energy from the specimen using the specimen itself and imaging hardware;
   determining features of the image for the specimen by inputting the image into two or more encoder layers of a neural network, wherein the image is a low resolution image of the specimen, wherein the neural network is configured as a deep generative model, and wherein the neural network does not comprise a fully connected layer thereby eliminating constraints on size of the image input to the two or more encoder layers; and
generating one or more simulated images from the determined features, wherein generating the one or more simulated images is performed by two or more decoder layers of the neural network, wherein the one or more simulated images are one or more high resolution images of the specimen, wherein said acquiring, said determining, and said generating are performed by one or more computer systems, wherein one or more components are executed by the one or more computer systems, and wherein the one or more components comprise the neural network.

* * * * *